US008426156B2

(12) United States Patent
Cubizolles et al.

(10) Patent No.: US 8,426,156 B2
(45) Date of Patent: Apr. 23, 2013

(54) METHOD FOR ASSAYING PLASMA ENZYMES IN WHOLE BLOOD

(75) Inventors: Myriam-Laure Cubizolles, Grenoble (FR); Marie-Line Cosnier, Grenoble (FR); Magalie Faivre, Grenoble (FR); Patrick Pouteau, Meylan (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 129 days.

(21) Appl. No.: 12/763,395

(22) Filed: Apr. 20, 2010

(65) Prior Publication Data

US 2011/0104712 A1    May 5, 2011

(30) Foreign Application Priority Data

Apr. 20, 2009  (FR) ..................................... 09 01894

(51) Int. Cl.
*C12Q 1/32* (2006.01)
(52) U.S. Cl.
USPC .......................................................... 435/26
(58) Field of Classification Search ................ 435/4, 15, 435/16, 26
See application file for complete search history.

(56) References Cited

U.S. PATENT DOCUMENTS

| 3,925,162 A | 12/1975 | Kanno |
| 2002/0160518 A1* | 10/2002 | Hayenga et al. ................. 436/70 |
| 2010/0248278 A1* | 9/2010 | Pouteau et al. .................. 435/13 |

OTHER PUBLICATIONS

Steigert J. et al. Integrated Siphon Based Metering and Sedimentation of Whole Blood on a Hydrophilic Lab-On-A-Disk. Biomedical Microdevices 9:675-679, 2007.*
Marcos S. et al. Intrinsic Molecular Fluorescence of Lactate Dehydrogenase . . . Analyst 122(4)355-359 Apr. 1997.*
Schumann G. IFCC Primary Reference Procedures for the Measurement of Catalytic Activity Concentrations of Enzymes at 37 Degrees C. Clinical Chemistry Lab Medicine 40(7)725-733, 2002.*
Schumann G. et al. IFCC Primary Reference Procedures . . . Clinical Chemistry Lab Medicine 40(7)718-724, 2002.*
Zhuang et al., "Microchip-based capillary electrophoresis for determination of lactate dehydrogenase isoenzymes," *Journal of Separation Science*, vol. 30, No. 9, Jun. 2007, pp. 1350-1356.
Huang et al., "Aspartate Aminotransferase (AST/GOT) and Alanine Aminotransferase (ALT/GPT)) Detection Techniques," *Sensors*, vol. 6, No. 31, Jul. 31, 2006, pp. 756-782.
Search Report for French Application No. 0901894 dated Nov. 4, 2009.

* cited by examiner

*Primary Examiner* — Ralph Gitomer
(74) *Attorney, Agent, or Firm* — Alston & Bird LLP (57) ABSTRACT

The present invention relates to a method for assaying catalytic plasma enzymes, such as transaminases and NADH-dependent enzymes, in a sample of whole blood, by measuring, in a microfluidic chamber, the decrease in the fluorescence of NADH consumed during the enzymatic reactions catalyzed by the NADH-dependent enzymes.

15 Claims, 10 Drawing Sheets

| Ht, % | Patient | ALT by HCL, U/l | Raw data Rep#1 | Rep#2 | Rep#3 | ABS mean | Standard deviation | CV | Normalized data Rep#1 | Rep#2 | Rep#3 | Mean | Standard deviation | Subtracted normalized data Rep#1 | Rep#2 | Rep#3 | Mean | Standard deviation |
|---|---|---|---|---|---|---|---|---|---|---|---|---|---|---|---|---|---|---|
| 32% | 1 | 30 | -8.3 | -7.9 | -8.3 | 8.2 | 0.2 | 3.0% | -2.0% | -1.9% | -1.6% | 1.8% | 0.2% | -1.0% | -1.0% | -0.7% | 0.9% | 0.2% |
| 37% | 2 | 14 | -6.4 | -5.0 | -5.0 | 5.5 | 0.8 | 14.7% | -1.5% | -1.2% | -1.2% | 1.3% | 0.2% | -0.6% | -0.3% | -0.3% | 0.4% | 0.2% |
| 46% | 3 | 20 | -6.9 | -5.4 | -6.2 | 6.2 | 0.7 | 12.0% | -1.7% | -1.5% | -1.7% | 1.6% | 0.1% | -0.8% | -0.6% | -0.8% | 0.8% | 0.1% |
| 29% | 4 | 32 | -8.7 | -8.0 | -8.4 | 8.4 | 0.4 | 4.3% | -2.4% | -2.3% | -2.4% | 2.3% | 0.1% | -1.6% | -1.4% | -1.5% | 1.5% | 0.1% |
| 30% | 5 | 104 | -19.4 | -23.9 | -19.0 | 20.8 | 2.7 | 13.0% | -6.1% | -6.9% | -5.9% | 6.3% | 0.5% | -5.3% | -6.0% | -5.1% | 5.5% | 0.5% |
| 38% | 6 | 16 | -6.5 | -7.6 | -5.8 | 6.6 | 0.9 | 13.3% | -1.5% | -1.4% | -1.4% | 1.4% | 0.1% | -0.7% | -0.6% | -0.5% | 0.6% | 0.1% |
| 43% | 7 | 23 | -6.6 | -6.5 | -7.0 | 6.7 | 0.2 | 3.6% | -1.6% | -1.5% | -1.6% | 1.6% | 0.1% | -0.7% | -0.7% | -0.8% | 0.7% | 0.1% |
| 46% | 8 | 40 | -9.0 | -9.9 | -9.6 | 9.5 | 0.5 | 5.1% | -2.2% | -2.2% | -2.1% | 2.2% | 0.1% | -1.3% | -1.4% | -1.3% | 1.3% | 0.1% |
| 38% | 9 | 24 | -6.5 | -7.0 | -6.8 | 6.8 | 0.2 | 3.6% | -1.6% | -1.7% | -1.6% | 1.6% | 0.0% | -0.7% | -0.8% | -0.8% | 0.8% | 0.0% |
| 28% | 10 | 63 | -13.7 | -14.5 | -14.2 | 14.1 | 0.4 | 3.0% | -3.3% | -3.5% | -3.4% | 3.4% | 0.1% | -2.5% | -2.6% | -2.6% | 2.6% | 0.1% |
| 39% | 11 | 12 | -5.6 | -4.5 | -4.6 | 4.9 | 0.6 | 13.0% | -1.4% | -1.2% | -1.2% | 1.3% | 0.1% | -0.6% | -0.3% | -0.3% | 0.4% | 0.1% |
| 33% | 12 | 16 | -6.0 | -6.4 | -7.3 | 6.5 | 0.7 | 10.4% | -1.4% | -1.6% | -1.6% | 1.5% | 0.1% | -0.5% | -0.7% | -0.8% | 0.7% | 0.1% |
| 39% | 13 | 87 | -15.9 | -15.9 | -16.2 | 16.0 | 0.2 | 1.0% | -5.1% | -5.1% | -5.2% | 5.1% | 0.1% | -4.2% | -4.2% | -4.3% | 4.2% | 0.1% |
| 30% | 14 | 8 | -4.6 | -4.5 | -4.1 | 4.4 | 0.2 | 5.4% | -1.2% | -1.3% | -1.2% | 1.3% | 0.1% | -0.4% | -0.5% | -0.4% | 0.4% | 0.1% |
| 29% | 15 | 108 | -19.6 | -22.9 | -21.7 | 21.4 | 1.7 | 7.9% | -5.8% | -6.2% | -6.6% | 6.2% | 0.4% | -5.0% | -5.3% | -5.7% | 5.3% | 0.4% |
| 31% | 16 | 93 | -22.7 | -18.9 | -18.6 | 20.1 | 2.3 | 11.4% | -6.6% | -5.5% | -5.5% | 5.9% | 0.7% | -5.7% | -4.6% | -4.5% | 5.0% | 0.7% |
| 23% | 17 | 57 | -6.9 | -5.6 | -6.1 | 6.2 | 0.7 | 10.8% | -1.9% | -1.6% | -1.7% | 1.7% | 0.1% | -0.9% | -0.7% | -0.7% | 0.8% | 0.1% |
| 26% | 18 | 407 | -55.3 | -57.9 | -68.3 | 60.5 | 6.9 | 11.4% | -16.9% | -18.1% | -22.0% | 19.0% | 2.6% | -15.5% | -16.7% | -20.5% | 17.6% | 2.6% |
| 35% | 19 | 150 | -26.3 | -26.2 | -23.7 | 25.4 | 1.4 | 5.7% | -7.5% | -7.6% | -6.5% | 7.2% | 0.6% | -6.6% | -6.7% | -5.6% | 6.3% | 0.6% |
| 50% | 20 | 163 | -20.8 | -22.6 | -24.2 | 22.5 | 1.7 | 7.6% | -5.7% | -6.3% | -6.7% | 6.2% | 0.5% | -4.8% | -5.4% | -5.8% | 5.3% | 0.5% |
| 40% | 21 | 132 | -21.7 | -21.0 | -21.5 | 21.4 | 0.4 | 1.8% | -5.3% | -5.1% | -5.2% | 5.2% | 0.1% | -4.3% | -4.2% | -4.3% | 4.3% | 0.1% |
| 38% | 22 | 126 | -19.5 | -19.2 | -18.9 | 19.2 | 0.3 | 1.5% | -6.5% | -6.4% | -6.4% | 6.4% | 0.0% | -5.5% | -5.5% | -5.5% | 5.5% | 0.0% |
| 30% | 23 | 145 | -26.4 | -24.3 | -23.7 | 24.8 | 1.4 | 5.7% | -8.8% | -8.2% | -7.7% | 8.2% | 0.6% | -7.9% | -7.3% | -6.7% | 7.3% | 0.6% |
| 30% | 24 | 151 | -23.7 | -27.9 | -28.6 | 26.7 | 2.6 | 9.9% | -7.6% | -9.5% | -9.1% | 8.8% | 1.0% | -6.7% | -8.6% | -8.2% | 7.8% | 1.0% |
| 37% | 25 | 113 | -19.3 | -18.6 | -18.5 | 18.8 | 0.4 | 2.2% | -6.6% | -6.3% | -6.7% | 6.5% | 0.2% | -5.7% | -5.4% | -5.7% | 5.6% | 0.2% |
| | | | | | Slope | 0.140 | Min | 1.0% | | | Slope | 0.0455% | | | | Slope | 0.044% | |
| | | | | | Intercept | 3.727 | Max | 14.7% | | | Intercept | 0.709% | | | | Intercept | -0.096% | |
| | | | | | R² | 0.976 | CV | 8.1% | | | R² | 0.963 | | | | R² | 0.960 | |

METHOD FOR ASSAYING PLASMA ENZYMES IN WHOLE BLOOD

This application claims benefit of priority to application France 09 01894 filed Apr. 20, 2009.

FIELD OF THE INVENTION

The present invention relates to a method for assaying in vitro plasma enzymes, such as transaminases and NADH-dependent enzymes, in a biological liquid sample, by measuring the fluorescence of NADH.

BACKGROUND OF THE INVENTION

Transaminases are enzymes which catalyze the transfer of an amine group from one amino acid to another. In humans, two types of transaminases are distinguishable:

ASAT (ASpartate Amino Transferase), AST or GOT (Glutamate Oxaloacetic Transaminase). This enzyme catalyzes the following reaction (i): L-aspartate+α-ketoglutarate→oxaloacetate+L-glutamate;

ALAT (ALanine Amino Transferase), ALT or GPT (Glutamate Pyruvate Transaminase). This enzyme catalyzes the following reaction (ii): L-alanine+α-ketoglutarate→pyruvate+L-glutamate.

Transaminases are present in all tissues, mainly in the liver and the cardiac muscle, and in the red blood cells. In the event of hepatic damage (necrosis or hepatitis) or myocardial infarction for example, transaminases are released from the liver or the myocardium, respectively, into the bloodstream, causing an increase in the levels thereof in the blood. The assay of transaminases in the serum or the plasma of patients constitutes a tool for the diagnosis of hepatic and cardiac pathologies.

The principal methods for assaying plasma transaminases are based on optical, electrochemical, chromatographic or radiochemical methods (for a review see Huang et al., Sensors, 2006, 6:756-782). Optical methods are routinely used; among these methods, there may be mentioned:

Colorimetry:

This assay method is carried out using serum or plasma. After stopping the enzymatic reactions catalyzed by AST or ALT, a diazonium salt is used which reacts not only with oxaloacetate (one of the products of the reaction catalyzed by AST) to give a compound that is red in color, but also with L-glutamate (one of the products of the reactions catalyzed by AST and ALT) to give, in the presence of glutamate dehydrogenase, a compound that is green in color; the optical density (OD) of the red- or green-colored plasma or serum is then simply measured. The Beer-Lambert law then makes it possible to link the optical density of a solution to its molar concentration (c): OD=εlc, "ε" being the specific coefficient of absorption of the colored compound and "l" the thickness of the cuvette containing the solution (serum or plasma). The disadvantages of this method are mainly the calibration of the cuvettes which has to be carried out for each assay and requires stopping the enzymatic reactions in order to carry out the assay. It is also possible to use this method after immobilizing the reagents on a solid phase, for example on a membrane. Various devices for assaying transaminases, based on a colorimetric method after immobilization of the reagents on a solid phase, have been proposed. Among these devices, there may be mentioned the point-of-care biological device called Cholestech LDX® (Cholestech). The assay of AST and ALT transaminases using this device is carried out on a sample of 35 μL of capillary whole blood, and comprises the following steps: the blood is deposited in the well of a (disposable) cartridge (of the device) and migrates by capillarity in the cartridge which comprises a filter specifically retaining the red blood cells; the resulting plasma is then brought into contact with dry reagents on a membrane, leading to a colorimetric reaction; the optical system of the device then measures the intensity of the final color of the reaction by reflectance photometry, the blue coloration measured having an intensity proportional to the concentration of transaminases present in the sample (international applications WO 2004/90555 and WO 2005/044429);

UV Absorption Spectrophotometry at 340 nm:

According to this method, it is the activity of enzymes which degrade oxaloacetate and pyruvate, produced by AST and ALT respectively, which is measured during secondary enzymatic reactions. These enzymatic reactions are respectively catalyzed by the enzymes MDH (Malate DeHydrogenase; EC 1.1.1.37) and LDH (Lactate DeHydrogenase; EC 1.1.1.27), in the presence of NADH (β-nicotinamide adenine dinucleotide):

MDH catalyzes the following reaction (iii): oxaloacetate+NADH+H$^+$→malate+NAD$^+$;

LDH catalyzes the following reaction (iv): pyruvate+NADH+H$^+$→L-lactate+NAD$^+$.

NADH (reduced form) absorbs in the ultraviolet (UV) region at 340 nm, whereas NAD$^+$ (oxidized form) does not absorb at this wavelength. It is therefore possible to measure the enzymatic activity of the side reactions catalyzed by LDH or MDH by monitoring the decrease in UV absorbance at 340 nm (corresponding to the consumption of NADH during the enzymatic side reactions as a function of time), and thus deduce therefrom the enzymatic activities of AST and ALT. The assay of the transaminases AST and ALT by this method is carried out, not directly on whole blood, but on serum or plasma (Karmen et al., J. Clin. Invest., 1955, 34:131-133; U.S. Pat. No. 3,925,162 and European patent application EP 415 188). Indeed, whole blood, which comprises red blood cells, is a very absorbent medium, in particular at the wavelength of 340 nm, and variable levels of hematocrit (defined as the ratio, expressed as a percentage, between the volume of red blood cells obtained by centrifuging a sample of whole blood and the volume of this sample) of different patients exhibiting moreover an identical transaminase level could give rise to different transaminase assay results because the variation in UV absorption is thought to be a function of the quantity of red blood cells and not a function of the level of transaminases. In accordance with the recommendations of the IFCC (International Federation of Clinical Chemistry and Laboratory Medicine), the assay of AST according to this method comprises the following steps: mixing the plasma or the serum with L-aspartate, NADH, pyridoxal phosphate (PPal or PLP for pyridoxal-phosphate), an MDH and an LDH in an appropriate buffer; the mixture is incubated for 5 minutes; α-ketoglutarate is then added (so as to initiate the enzymatic reaction (i) above; the mixture is allowed to incubate for 90 seconds; and the decrease in UV absorbance of NADH is measured for 180 seconds (Schumann et al., Clin. Chem. Lab. Med., 2002, 40:725-733). A latency (or incubation) phase of 90 seconds is recommended in order to obtain a linear decrease in the signal (UV absorbance) measured as a function of time. In accordance with the IFCC recommendations, the assay of ALT according to this method comprises the same steps as those described for the AST assay, but no MDH is used and L-aspartate is replaced with L-alanine; the addition of α-ketoglutarate makes it possible to initiate the enzymatic reaction (ii) above (Schumann et al., Clin. Chem. Lab. Med., 2002, 40:718-724).

Fluorescence:

This method involves the same enzymatic side reactions as those described for UV absorption spectrophotometry above. NADH, excited at a wavelength of 340 nm, fluoresces at a wavelength of 460 nm, which is not the case for its oxidized form, $NAD^+$. The intensity of emission is then dependent on the concentration of NADH in the medium studied. The enzymatic activity of the transaminases AST and ALT can therefore be monitored by the reduction in the fluorescence emitted by NADH at 460 nm, either in a homogeneous phase, or after immobilization on a solid support. For the same reasons set out above, the assay of the transaminases AST and ALT by this method can only be carried out on serum or plasma (U.S. Pat. No. 3,925,162 and U.S. Pat. No. 5,612,178; international application WO 91/013169).

The assay of the plasma enzymes which have NADH as cofactor (NADH-dependent enzymes), such as LDHs and MDHs, is carried out, on serum or plasma, by measuring their enzymatic activity by NADH UV absorption spectrophotometry at 340 nm or by monitoring the reduction in the fluorescence at 460 nm of the NADH consumed during the enzymatic reaction catalyzed by these enzymes (in the case of the assay of MDH, it is the NADH consumed during the enzymatic reaction (iii) described above which is measured and in the case of the assay of LDH, it is the NADH consumed during the enzymatic reaction (iv) described above which is measured). The assay of these enzymes is performed by mixing the serum or plasma sample, their substrates (including NADH).

The assaying of LDHs, for example, is used for the diagnosis and monitoring of hepatic and cardiac conditions, and of certain cancers (lung and kidney cancers).

SUMMARY OF THE INVENTION

The inventors set themselves the aim of providing a method for assaying plasma enzymes, in particular NADH-dependent enzymes and transaminases, on a small volume (a few microliters) of human whole blood and without preliminary separation of the red blood cells, the assay being carried out rapidly after collecting the blood sample (10 to 30 minutes).

Surprisingly, the inventors have demonstrated that the assay of NADH-dependent catalytic plasma enzymes, such as LDHs and MDHs, by measuring their enzymatic activity (or catalytic concentration), can be carried out directly in a sample of whole blood, that is to say in the presence in particular of red blood cells, by measuring, in a microfluidic chamber, the decrease in the fluorescence of the NADH consumed during the enzymatic reaction catalyzed by these enzymes. This method has been found to be reliable, rapid and robust. In addition, it may be carried out with the aid of a point-of-care biological device.

This method may also be applied to the assay of a catalytic plasma enzyme $E_C$ having as substrates $S_1$ and $S_2$, such as transaminases, by measuring the decrease in the fluorescence of the NADH consumed during enzymatic side reactions which are catalyzed by one or more NADH-dependent catalytic enzymes which have for substrate one of the products of the enzymatic reaction catalyzed by said catalytic plasma enzyme $E_C$.

Consequently, the subject of the present invention is a method for assaying, in a biological liquid sample, an NADH-dependent catalytic plasma enzyme, by measuring its enzymatic activity, comprising a step of measuring the decrease in the fluorescence of the NADH, which method is characterized in that said biological liquid is whole blood and in that the enzymatic activity of said catalytic enzyme is measured by monitoring the decrease in the fluorescence of the NADH in a microfluidic chamber having a thickness of 20 µm to 2 mm.

The expression NADH-dependent catalytic plasma enzyme $(E_N)$ is understood to mean a catalytic enzyme present in the blood which uses NADH as cofactor.

By way of nonlimiting examples of NADH-dependent catalytic plasma enzymes $(E_N)$, there may be mentioned lactate dehydrogenase (LDH), malate dehydrogenase (MDH) and isocitrate dehydrogenase (IDH).

The expression microfluidic chamber is understood to mean a device having a fluid vein capable of receiving very small quantities of liquid sample, of the order of about ten microliters. The small dimensions of said chamber, from 20 µm to 2 mm thick, preferably from 20 µm to 100 µm, more preferably from 30 µm to 50 µm, and particularly 30 µm, make it possible to minimize movements in the liquid sample and allow the red blood cells to sediment within a few minutes depending on the thickness of the microfluidic chamber. Indeed, a characteristic feature of whole blood is the phenomenon of sedimentation due to gravity acting on the most dense particles, the rate of sedimentation of the red blood cells being between 0.3 and 3 µm/s. It is therefore advantageous to choose a microfluidic chamber of a few tens of µm thick so as to have the shortest possible sedimentation time (or latent time).

Any material which is transparent to wavelengths of about 300 to 550 nm, such as plastic and quartz, may be used to manufacture the microfluidic chamber.

According to another advantageous embodiment of the invention, said microfluidic chamber comprises two walls, preferably of low thickness (of about one hundred µm to a few mm), substantially parallel and separated by one or more means of keeping apart, such that the distance between said two walls is between 20 µm and 2 mm, preferably between 20 µm and 100 µm, more preferably between 30 µm and 50 µm, and particularly 30 µm. The means for keeping apart may be, without limitation, continuous or discontinuous blocks or bars.

According to an advantageous feature of this embodiment of the invention, said microfluidic chamber comprises at least one wall consisting of a material reflecting fluorescence light. The use of a material which reflects fluorescence light makes it possible, despite the accumulation of the red blood cells at the bottom of said microfluidic chamber, to increase the fluorescence signal measured. Said reflective material may consist of silicon oxides or nitrides, such as $SiO_3$ and $Si_3N_4$, or silicon $(SiO_2)$, preferably silicon.

According to another advantageous feature of this embodiment of the invention, said microfluidic chamber comprises a substantially flat wall, made of glass or silicon, such as for example a microscope slide, and a wall which is also substantially flat, made of quartz or plastic, such as for example a microscope cover glass; said walls being spaced apart by 20 µm to 2 mm, preferably 20 µm to 100 µm, more preferably 30 µm to 50 µm, and particularly 30 µm, with the aid of blocks (or spacers) for example.

The sample of whole blood, preferably human blood, may be collected over an anticoagulant, such as EDTA (ethylenediaminetetracetic acid), sodium citrate or heparin, preferably sodium citrate.

According to another advantageous embodiment of the invention, the volume of the whole-blood sample is between 0.1 µL and 50 µL, preferably it is 3 µL.

Said whole-blood sample may also be mixed with the substrates of said NADH-dependent catalytic plasma enzyme (including NADH) and with an appropriate buffer. Such buffers are well known to persons skilled in the art. By way of examples of buffers, there may be mentioned Tris(hydroxymethyl)aminomethane (Tris) and a mixture consisting of Tris and sodium azide (NaN$_3$).

The whole-blood sample may be introduced into said microfluidic chamber with the aid of a pump or a piston, or by capillary migration, while avoiding the lysis of the red blood cells (hemolysis). Indeed, the red blood cells may contain enzymes identical to said catalytic enzymes and which must not be assayed (given that it is desired to determine the catalytic activity of the plasma enzymes).

According to another advantageous embodiment of the invention, 20 µM to 250 µM of NADH are added to said whole-blood sample.

The fluorescence of NADH is measured with the aid of a fluorimeter or an appropriate camera, sensitive to fluorescence, at a wavelength of between 420 nm and 550 nm, preferably at 460 nm, after excitation of the NADH at a wavelength of between 300 nm and 400 nm.

According to a preferred embodiment of the invention, the measurement of the decrease in fluorescence is carried out after a latent time has elapsed, time defined by the sedimentation time of the red blood cells in said microfluidic chamber; this latent time therefore varies according to the thickness of said microfluidic chamber.

According to another advantageous embodiment of the invention, the measurement of the decrease in the fluorescence of NADH is carried out at room temperature or at a temperature of about 37° C., preferably at 37° C.

The decrease in the fluorescence of NADH may be measured for 180 seconds after the latent period has elapsed.

The subject of the present invention is also a method for assaying, in a sample of biological liquid, a catalytic plasma enzyme ($E_C$) having $S_1$ and $S_2$ as substrates, by measuring the enzymatic activity of said enzyme $E_C$, comprising at least the following steps: a) incubation of said biological liquid with said substrate $S_1$, NADH, one or more different NADH-dependent catalytic enzymes ($E_N$) each having as substrate one of the products of the enzymatic reaction catalyzed by $E_C$, and optionally pyridoxal phosphate; b) addition of said substrate $S_2$ so as to initiate the enzymatic reactions catalyzed by the catalytic enzymes $E_C$ and $E_N$; which method is characterized:

in that said biological liquid is whole blood, as defined above, in that after the addition of the substrate $S_2$ in step b), the mixture obtained is immediately introduced into a microfluidic chamber 20 µm to 2 mm thick as defined above, and in that the enzymatic activity of said catalytic enzyme $E_C$ is measured by monitoring the decrease in the fluorescence of NADH in said microfluidic chamber, under the conditions defined above.

According to an advantageous embodiment of this aspect of the invention, said microfluidic chamber has a thickness of a few tens of µm. Indeed, in the case of the use of a microfluidic chamber having a thickness of 30 µm for assaying transaminases, the distance covered by the red blood cells for a complete sedimentation in said microfluidic chamber is up to about 27 µm during the 90 seconds of the latent period, which corresponds to the recommended latent period.

According to another advantageous embodiment of this aspect of the invention, the concentration of NADH in the mixture obtained in step a) is 20 µM to 250 µM.

The incubation time in step a) defined above is between 2 and 30 minutes, preferably it is 5 minutes.

Said catalytic enzyme ($E_C$) defined above may be any catalytic plasma enzyme for which one of the products obtained during the enzymatic reaction catalyzed by it is itself a substrate of at least one catalytic enzyme ($E_N$) having NADH as cofactor. By way of example of catalytic enzymes ($E_C$), there may be mentioned aspartate aminotransferase (AST), alanine aminotransferase (ALT), pyruvate kinase, creatine kinase and glycerol kinase. The enzymatic activity of these enzymes may be measured using a lactate dehydrogenase (LDH) and/or a malate dehydrogenase (MDH) as catalytic enzyme $E_N$.

LDHs (EC 1.1.1.27) and MDHs (EC 1.1.1.37) are well known to persons skilled in the art. They may be isolated from any mammal, preferably pigs, or they may be recombinant or synthetic.

According to one particular embodiment of this aspect of the invention, said catalytic enzyme $E_C$ is aspartate aminotransferase.

According to this particular embodiment of the invention, said substrate $S_1$ is L-aspartate, said substrate $S_2$ is α-ketoglutarate, and said catalytic enzymes $E_N$ are either an MDH, or an MDH and an LDH; the concentration of NADH in the mixture obtained in step a) is preferably 20 to 200 µM, more preferably 90 µM; and the fluorescence of NADH is preferably measured at 460 nm after excitation of NADH at a wavelength of preferably 318 nm.

According to another particular embodiment of this aspect of the invention, said catalytic enzyme $E_C$ is alanine aminotransferase.

According to this particular embodiment of the invention, said substrate $S_1$ is L-alanine, said substrate $S_2$ is α-ketoglutarate, and said catalytic enzyme $E_N$ is an LDH; the concentration of NADH in the mixture obtained in step a) is preferably 20 to 250 µM, more preferably 180 µM; and the fluorescence of NADH is preferably measured at 460 nm after excitation of the NADH at a wavelength of preferably 367 nm.

The concentration of AST or of ALT in the blood sample expressed in U/L is obtained by multiplying the value of the enzymatic activity (catalytic concentration) of AST or ALT expressed in µkat/l by a factor f equal to 60 (see the articles by Schumann et al., 2002, cited above).

The subject of the present invention is also the use of a microfluidic chamber as defined above, for assaying a catalytic plasma enzyme ($E_N$ or $E_C$) as defined above in a whole-blood sample.

The subject of the present invention is also a kit or box for assaying a catalytic plasma enzyme $E_C$, as defined above in a whole-blood sample, characterized in that it comprises a microfluidic chamber as defined above, and the following reagents: the substrates $S_1$ and $S_2$, NADH, at least one NADH-dependent catalytic enzyme ($E_N$), and optionally PLP.

According to one embodiment of the kit or box according to the invention, it comprises a microfluidic chamber as described above, L-Asp, an MDH, NADH, α-ketoglutarate and optionally an LDH and PLP, the kit or box being useful for measuring the enzymatic activity or assaying AST in a human whole-blood sample.

According to another embodiment of the kit or box according to the invention, it comprises a microfluidic chamber as described above, L-Ala, an LDH, NADH, α-ketoglutarate and PLP, the kit or box being useful for measuring the enzymatic activity or assaying ALT in a human whole-blood sample.

The subject of the present invention is also a kit or box for assaying an NADH-dependent catalytic plasma enzyme, characterized in that it comprises a microfluidic chamber as defined above.

BRIEF DESCRIPTION OF THE DRAWINGS

In addition to the preceding features, the invention also comprises other features which will emerge from the description which follows, and which refer to examples of carrying out the method which is the subject of the present invention, and to the accompanying drawings, in which:

FIG. 4 represents the detailed results of the assays of the transaminases ALT (figure A) and AST (figure B) in hospitalized patients. Figures A and B—the "Slope" value corresponds to the slope of the linear regression between the slope of the decrease in fluorescence and the transaminase activity measured according to the reference method. The "Intercept" value corresponds to the ordinate at the origin of this same linear regression. "$R^2$" is the linear regression determination coefficient. The "Min" value represents the minimum value of the CV (coefficient of variation), while the "Max" value represents the maximum value of the CV. "$CV_p$" corresponds to the "pooled" CV, calculated according to the following formula: $CV_p = \sqrt{((CV_1^2 + CV_2^2 + \ldots + CV_n^2)/n)}$. Ht=hematocrit. ALT or AST by HCL=enzymatic activity measured with the aid of the automated machine of the COBAS range (Roche) operating by measuring the UV absorbance of NADH at 339 nm. Rep=repeat. ABS mean=absolute value of the mean of the three experiments. Figure B—the values marked * correspond to the results obtained with 90 µM of NADH and a latent period of 90 seconds. The values marked  correspond to the results obtained with 45 µM of NADH and a latent period of 90 seconds, and the values marked * correspond to the results obtained with 90 µM of NADH and a latent period of 30 seconds.

DETAILED DESCRIPTION

Example 1

Assay of Transaminases by Measuring the Decrease in the Fluorescence of NADH in the Human Whole-Blood Sample: Study of Various Parameters Capable of Influencing the Reliability and Repeatability of the Measurements 1.1 Materials and methods
a) Reagents Used:
- L-alanine (L-Ala): free of acid, BioUltra, ≧99.5% (NT), Fluka, Ref: 05129;
- L-aspartate (L-Asp): free of acid, BioUltra, ≧99.5% (T), Fluka, Ref: 11189;
- pyridoxal 5'-phosphate monohydrate (PLP): BioChemika, ≧97.0% (NT), Fluka, Ref: 82870;
- α-ketoglutarate: disodium salt dihydrate of α-ketoglutaric acid, purity≧98.5% (dry matter, NT), Fluka, Ref: 75892;
- lactate dehydrogenase (LDH): EC 1.1.1.27, obtained from pig skeletal muscle, in glycerol, homotetramer, Roche, Ref: 10 127 221 001;
- malate dehydrogenase (MDH): EC 1.1.1.37, obtained from pig heart, in glycerol, homodimer, Roche, Ref: 10 127 892 001;
- alanine aminotransferase (ALT): glutamate-pyruvate transaminase (GPT), obtained from pig heart, freeze-dried powder, ≧75 units/mg of protein, Sigma, Ref: G8255;
- aspartate aminotransferase (AST): glutamate oxaloacetate transaminase (GOT), obtained from pig heart, type II-A, freeze-dried powder, 100-400 units/mg of protein, Sigma, Ref: G7005;
- BSA: "Bovine Serum Albumin", fraction V, ≧98% (agarose gel electrophoresis), essentially free of protease, freeze-dried powder, Sigma, Ref: A3294;
- sodium chloride (NaCl): Sigma, Ref: S9625;
- NADH: disodium salt of β-nicotinamide adenine dinucleotide in reduced form, Sigma, Ref: N8129;
- Tris: Tris(hydroxymethyl)aminomethane, Sigma, Ref: T1503;

NaN₃: sodium azide, ReagentPlus®, ≧990%, Sigma-Aldrich, Ref: S2002.

b) Preparation of the Solutions for the Enzymatic Reactions:

Solutions for the Assay of AST (Stored at 4° C.):
  solution 1 (5 ml): Tris 96.92 mM pH 7.65, L-Asp 302.4 mM, NaN₃ 8 mM
  solution 2 (50 µL): Tris 96.92 mM pH 7.65, NaN₃ 8 mM
  solution 3 (100 µL): PLP 6.3 mM
  solution 4 (50 µL): NADH 11.34 mM
  solution 5 (50 µL): LDH 113.4 U/ml, MDH 75.6 U/ml
  reaction solution: solution 1+solution 2+solution 3+solution 4+solution 5

Solutions for the Assay of ALT (Stored at 4° C.):
  solution 1(5 ml): Tris 121.2 mM pH 7.15, L-Ala 630 mM, NaN₃ 8 mM
  solution 2 (50 µL); Tris 121.2 mM pH 7.15, NaN₃ 8 mM
  solution 3 (100 µL): PLP 6.3 mM
  solution 4 (50 µL): NADH 11.34 mM
  solution 5 (50 µL): LDH 214 U/mL
  reaction solution: solution 1+solution 2+solution 3+solution 4+solution 5 c) Manufacture of the Microfluidic Chambers:

The fluidic chambers were manufactured with a thickness of 30 µm (this thickness makes it possible to sediment all the red blood cells in the chamber within 90 seconds before measuring the fluorescence). The base of the fluidic chambers consisted either of a glass slide with the standard format of a microscope slide, or a silicon slide of the same format. Double sided adhesive tape 30 µm thick was then applied to the block (pellet) on the base slide. Next, a microscope cover glass made of quartz was applied to the adhesive tape, so as to form the microfluidic chamber. The use of quartz allows the detection of the fluorescence of NADH while being transparent to ultraviolet radiation ($\lambda_{ex}$ of NADH=320 nm-370 nm). The microfluidic chambers were placed on the stage of a microscope (Olympus BX60 combined with an Omega XF06 optical filter), which was either at room temperature, or thermostated at 37° C.

d) Protocol for Measuring the Fluorescence

3 µL of human whole blood was mixed with 30 µL of reaction solution containing all the reagents necessary for the assay (except α-ketoglutarate). The mixture thus obtained was incubated for 5 min at 37° C. or at room temperature. 3 µL of an α-ketoglutarate solution (144 mM for the assay of AST or 180 mM for the assay of ALT) were then added to the reaction mixture in order to initiate the enzymatic reaction. After rapid stirring, 20 µL of the mixture were immediately deposited at the inlet of the microfluidic chamber, which fills up by capillarity. After introducing the reaction mixture into the microfluidic chamber, the latent period of 90 seconds at 37° C. or at room temperature begins. Once the latent period has elapsed, the reaction mixture was excited at a wavelength of 318 (for the AST assay) or 367 nm (for the ALT assay), with the aid of a filtered 100 mW UV lamp (pass band of the filter 320 nm<λ<380 nm), and the kinetics of decrease of the fluorescence signal was measured for 180 seconds with the aid of a filtered (420 nm<λ<500 nm) ORCA camera (Hamamatsu); the opening and closing of the shutter and the acquisition of the images being performed autonomously, directly piloted by a computer. During the 180 s kinetics, the acquisition of the images occurred every 15 s, that is to say a collection of 13 photos in total. The shutter was opened and then closed at each capture of images, so as to limit photo-bleaching.

For the expression of the results, the fluorescence signal was normalized (the raw data are normalized to the same ordinate (100%) at the origin) and subtracted (subtraction from the straight line obtained from the normalized raw data, the straight line obtained on a "blank" sample in order to take into account the effect of the photo-bleaching).

The "blank" sample is a sample which does not contain transaminases or which contains transaminases but in which the reactions catalyzed by them are not initiated; there is therefore no consumption of NADH in said "blank" sample. The only decrease in fluorescence which is then observed is due to the photo-bleaching.

e) Reference Method

The results obtained using the method for assaying transaminases according to the present invention were compared to those obtained with the Cholestech LDX® system (Cholestech) using the protocol recommended by the manufacturer.

f) Calculation of the Photo-Bleaching

The photo-bleaching (%) was calculated on the "blank" sample as follows: [(intensity of fluorescence of the 1st measurement
  intensity of fluorescence of the 13th measurement)/(intensity of fluorescence of the 1st measurement)]×100.

1.2 Results 1.2.1. Effect of the Temperature

The effect of the temperature on the results obtained was checked. For this, a whole-blood sample obtained from a healthy donor from the Etablissement Français du Sang (EFS) was supplemented with porcine transaminases in order to obtain a range of concentration of transaminases, namely between 10 and 100 U/L for AST and between 20 and 200 U/L for ALT. The assay according to the Cholestech LDX® system of the 8 samples from the range prepared showed enzymatic activities of between 34 and 110 U/L for AST, and between 20 and 177 U/L for ALT. These same samples were then analyzed by the method according to the present invention which makes it possible to monitor the decrease in the fluorescence of NADH, either at room temperature (22° C.), or at 37° C., and using microfluidic chambers whose base consisted of glass. The blanks prepared for this experiment were made with a pellet of red blood cells which were washed so as to remove any trace of residual catalytic activity of the plasma transaminases.

Figure 1:
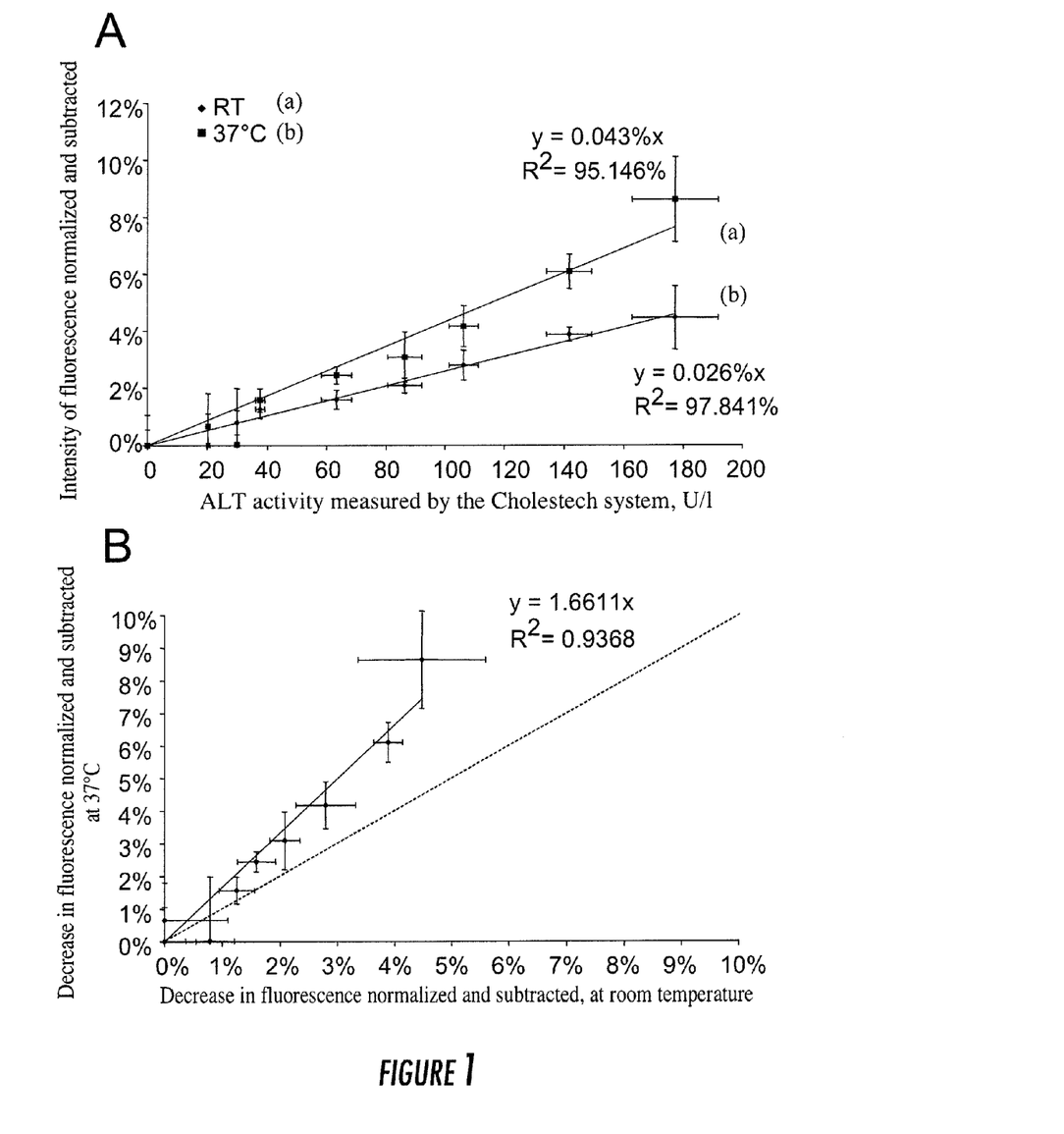
FIG. 1 represents the effect of temperature on the measurement of the decrease in the fluorescence of NADH for the assay of ALT. A—correlation between the reference method and the method according to the present invention at room temperature (a) or at 37° C. (b). B—correlation between the measurements according to the method of the present invention at room temperature and at 37° C.

The results for the ALT assay are presented in FIG. 1. FIG. 1A shows the correlations obtained between the reference method (Cholestech LDX® system) and the decrease in fluorescence after normalization of the data and subtraction of the "blank" sample. The two correlations show coefficients $R^2=0.978$ at 22° C. (room temperature) and $R^2=0.951$ at 37° C. It is evident from this figure that the decreases in fluorescence observed at 37° C. are greater than those obtained at room temperature, which is perfectly consistent because the enzymatic reactions are optimal at 37° C. The correlation between the measurements performed at 37° C., and those performed at room temperature, illustrated in FIG. 1B, shows this improvement in results: the values are increased by a factor of 1.66 at 37° C. compared with room temperature.

For this series of experiments at different temperatures, photo-bleaching does not appear to be affected by the temperature. This is consistent since the photo-bleaching of the fluorophore is essentially due to the time of exposure to the light beam and not to the temperature.

The measurement of the decrease in the fluorescence of NADH allowing monitoring of the enzymatic activity of transaminases can therefore be carried out at 37° C. or at room temperature, even though the temperature of 37° C. is optimal.

1.2.2. Effect of the Material of the Base of the Microfluidic Chamber (Glass or Silicon)

The decreases in fluorescence signal which are observed in glass microfluidic chambers were found to be 10% maximum for the highest transaminase levels (that is to say 200 U/L for ALT). At the excitation wavelengths used (between 300 and 400 nm), glass is absorbent. Part of the excitation signal may therefore be lost through absorption by the glass. The use of a reflective material would make it possible to overcome this loss. A study was therefore performed to determine if it was possible to increase these decreases in signal beyond this 10% limit, so as to improve the precision of the measurements.

Microfluidic chambers comprising a silicon base were therefore manufactured as described in paragraph 1.1.c) above. A blood sample obtained from a healthy donor from EFS was supplemented with porcine transaminases (see paragraph 1.2.1.). The assay according to the Cholestech LDX® system of the 8 samples of the range prepared showed enzymatic activities of between 35 and 108 U/L for AST, and between 27 and 223 U/L for ALT. These same samples were then assayed according to the method of the present invention at 37° C., in glass or silicon microfluidic chambers. The blanks prepared for this experiment were made with a pellet of washed red blood cells.

Figure 2:
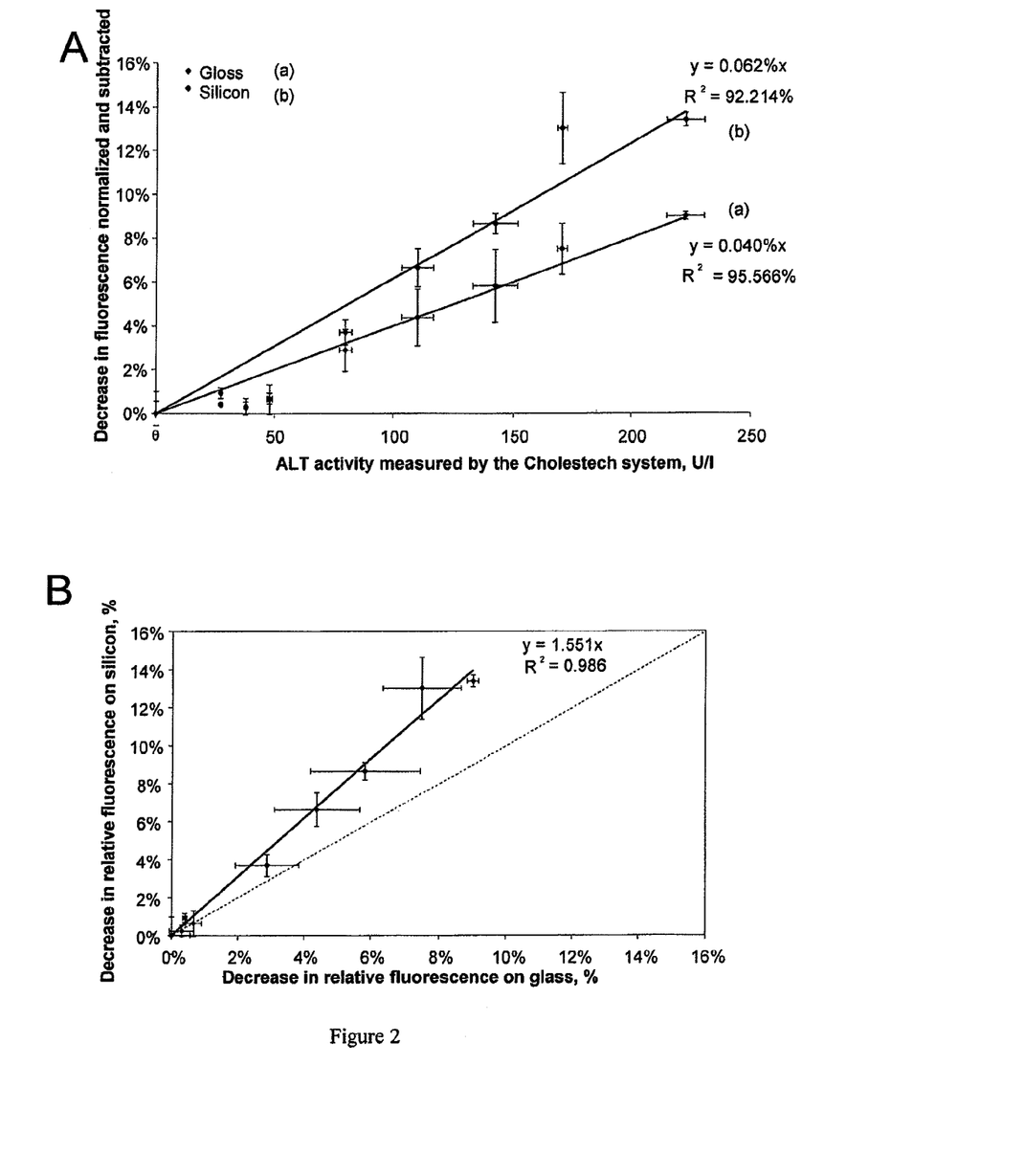
FIG. 2 represents the effect of the material constituting the base of the microfluidic chamber on the measurement of the decrease in the fluorescence of NADH for the assay of ALT. A—correlation between the reference method and the method according to the present invention with the bases of microfluidic chambers consisting of glass (a) or silicon (b). B—correlation between the measurements carried out with the bases of microfluidic chambers consisting of glass or silicon.

The results for the ALT assay are presented in FIG. 2. FIG. 2A shows the correlations obtained between the reference method and the measurement of the decrease in fluorescence (according to the method of the present invention) after normalization of the data and subtraction of the blank. The CVs observed for the experiments carried out with the glass bases of the microfluidic chambers are between 1.8% and 29.6%, while those obtained with the silicon bases of the microfluidic chambers are between 1.8 and 14.5%: the repeatability is therefore improved with silicon. Moreover, it is evident from this figure that the decreases in fluorescence which are observed with the silicon bases of the microfluidic chambers are greater than those observed on glass. The correlation between the measurements carried out with the glass bases of the microfluidic chambers, and those carried out with the silicon bases of the microfluidic chambers, illustrated in FIG. 2B, shows this improvement in the results: the values are increased by a factor of 1.6 with silicon compared with glass.

The photo-bleaching is less than 4% with glass, whereas it is less than 7% with silicon. This can be explained by the fact that the beam crosses the thickness of the microfluidic chamber twice, since it is reflected: the photo-bleaching is thus thereby increased.

Glass and silicon can therefore be used for the manufacture of the base of the microfluidic chambers. However, the use of silicon makes it possible to obtain greater decreases in signal compared with the use of glass, and the repeatability of the measurements is thereby improved.

1.2.3. Effect of the Concentration of NADH

A blood sample obtained from a healthy donor from EFS was supplemented with porcine transaminases at 8 different levels so as to establish an enzymatic activity range. The assay of transaminases was carried out with NADH concentrations of 90 µM or 180 µM. The assay according to the Cholestech LDX® system of the 8 samples from the range prepared showed enzymatic activities of between 32 and 125 U/L for AST, and between 19 and 228 U/L for ALT. These same samples were then analyzed by the method according to the present invention at 37° C., with microfluidic chambers whose base consisted of silicon. The blanks prepared for this experiment were made with a pellet of washed red blood cells.

Figure 3:
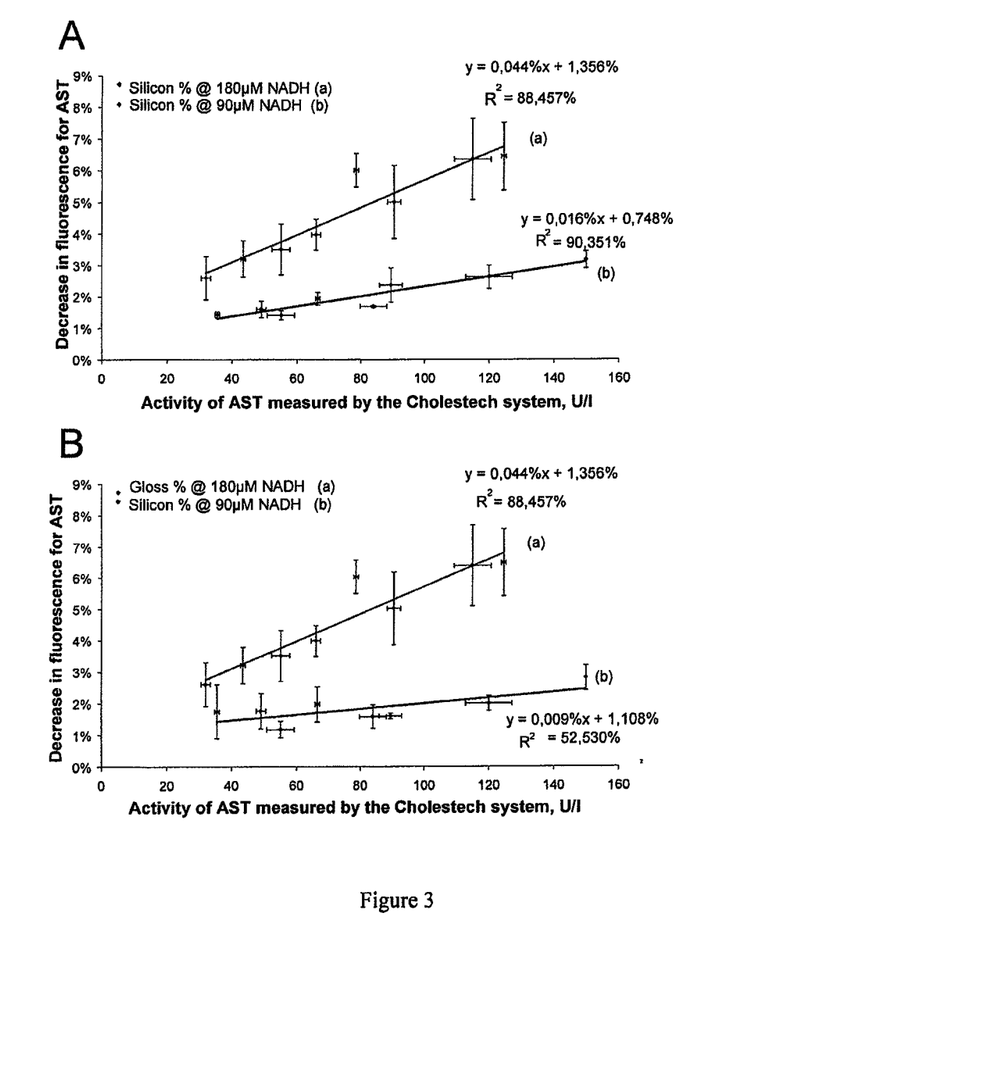
FIG. 3 represents the effect of the concentration of NADH on the measurement of the decrease in fluorescence for the assay of AST. A—correlation between the reference method and the method according to the present invention using 180 µM of NADH (a) or 90 µM of NADH (b). B—correlation between the measurements carried out with microfluidic chambers whose base consisted of glass or silicon and with respectively 180 µM (a) or 90 µM (b) of NADH.

The results of the AST assay are presented in FIG. 3. FIG. 3A shows the correlations obtained between the reference method and that according to the present invention after normalization of the data. The CVs observed at the two NADH concentrations are comparable, systematically below 30%. The two correlations show similar coefficients $R^2$, $R^2=0.903$ with 180 µM of NADH and $R^2=0.885$ with 90 µM of NADH. It is evident from this figure that the decrease in fluorescence observed with 90 µM of NADH is greater than that observed with 180 µM of NADH. The slopes of the linear regressions vary by a factor of 2.75.

FIG. 3B illustrates the improvement between the initial configuration, glass chamber and 180 µM of NADH, and the optimum configuration, silicon chamber and 90 µM of NADH. The variations in the decrease in fluorescence were improved practically by a factor of 5 between the two configurations.

For the AST assay, the use of 90 µM of NADH is found to be more reliable because it makes it possible to obtain larger variations in signal for the decrease in fluorescence.

Example 2

Experimental Validation of the Method for Assaying Transaminases by Measuring the Fluorescence of NADH The results presented in example 1 related to the assays carried out on blood samples obtained from healthy donors, which were supplemented with porcine transaminases in order to mimic the samples from sick patients, whose transaminase levels would be high. The method for assaying transaminases according to the present invention was then validated on whole-blood samples from sick patients collected over citrate.

Citrated blood samples obtained from patients hospitalized at the Hospices Civils de Lyons (HCL, France) were analyzed according to the method of the present invention. The measurements of the fluorescence of NADH were carried out according to the method described in example 1, with the following parameters:
  a temperature of 37° C.;
  microfluidic chambers with a silicon base;
  an NADH concentration of 180 µM for the assay of ALT and 90 µM for the assay of AST;
  measurements performed in triplicate;
  the "blanks" were prepared by replacing α-ketoglutarate (which initiates the enzymatic reaction) with an equivalent volume of 154 mM NaCl.

The results obtained by the measurement of the decrease in fluorescence according to the method of the present invention were compared to those obtained by the reference method used in the biochemistry laboratory of the Edouard Herriot hospital in Lyons (France). Table 1 below describes the main characteristics of the two methods:

TABLE 1

Comparison of the method for assaying the transaminases AST/ALT used by the biochemistry laboratory of the Edouard Herriot hospital Lyons with the aid of an automated machine of the Cobas range (Roche) and the method according to the present invention.

|  | Reference method | Method of the invention |
|---|---|---|
| Measurement system | Automated machine of the Cobas range from the company Roche operating by measuring the UV absorbance at 339 nm (decrease in NADH in the presence of PLP) | Experimental blank allowing the measurement of the decrease in the fluorescence of NADH at 460 nm (see example 1.1) |

TABLE 1-continued

Comparison of the method for assaying the
transaminases AST/ALT used by the biochemistry laboratory of
the Edouard Herriot hospital Lyons with the aid of an
automated machine of the Cobas range (Roche) and the method
according to the present invention.

|  | Reference method | Method of the invention |
|---|---|---|
| Volume of sample | 10 μL of heparinized plasma collected in a tube of 5 mL of centrifuged blood (3 μL of plasma if high level, 40 μL of plasma if low level) | 3 μL of citrated whole blood |
| Temperature | 37° C. | 37° C. |
| Number of replicates | 1 | 3 |
| Range | 4-600 U/L for ALT 4-800 U/L for AST | 20-200 U/L for ALT 10-100 U/L for AST |
| Duration of analysis | ~20 min of centrifugation + 10 min of passage through the automated machine ~30 min for a single measurement | 9 min 30 for a single measurement |
| Reproducibility | CV < 4% (intra- and inter-series) for ALT and AST | CV < 15% for ALT and CV < 25% for AST |

25 blood samples from different patients were analyzed for the assay of ALT, and 21 blood samples from different patients were analyzed for the assay of AST. The crude results are represented in FIG. 4.

2.1. Estimation of the Photo-Bleaching

During the kinetics of the enzymatic reactions (180 seconds), photos were taken every 15 seconds, with opening then closing of the shutter at each shot. A 10× lens was used and the exposure time was 50 milliseconds for an electron amplification factor of the optical signal of 250 (which is detected at the camera level).

Figure 5:
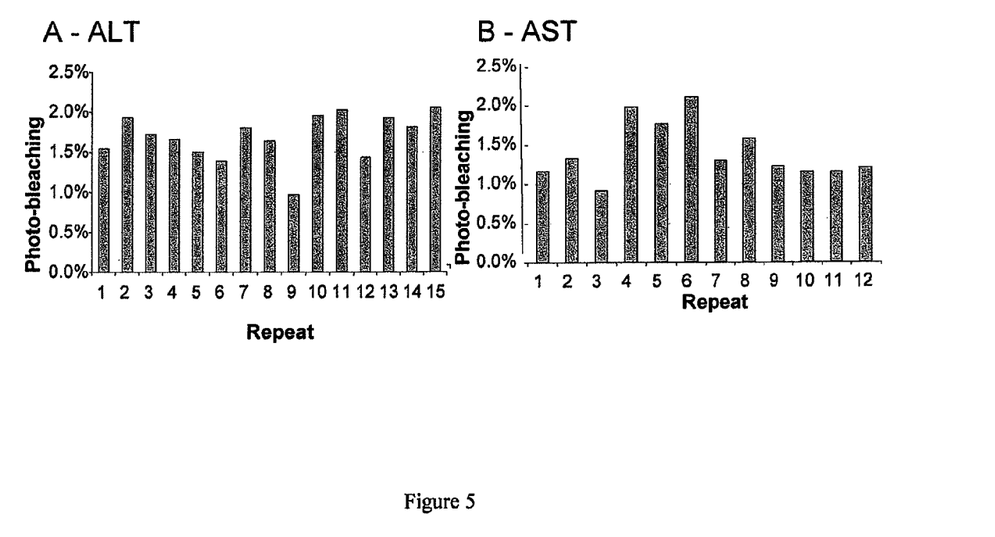
FIG. 5 represents the photo-bleaching values observed for assaying the transaminases ALT (figure A) and AST (figure B) by monitoring the decrease in the fluorescence of NADH.

The photo-bleaching (calculated according to the method described in example 1.1.f) above) was estimated on the measurements carried out on the "blank" samples. The results, presented in FIG. 5, show that the photo-bleaching is systematically less than 2% for this series of experiments where the "blank" samples are prepared by replacing α-ketoglutarate by 154 mM NaCl.

Figure 6:
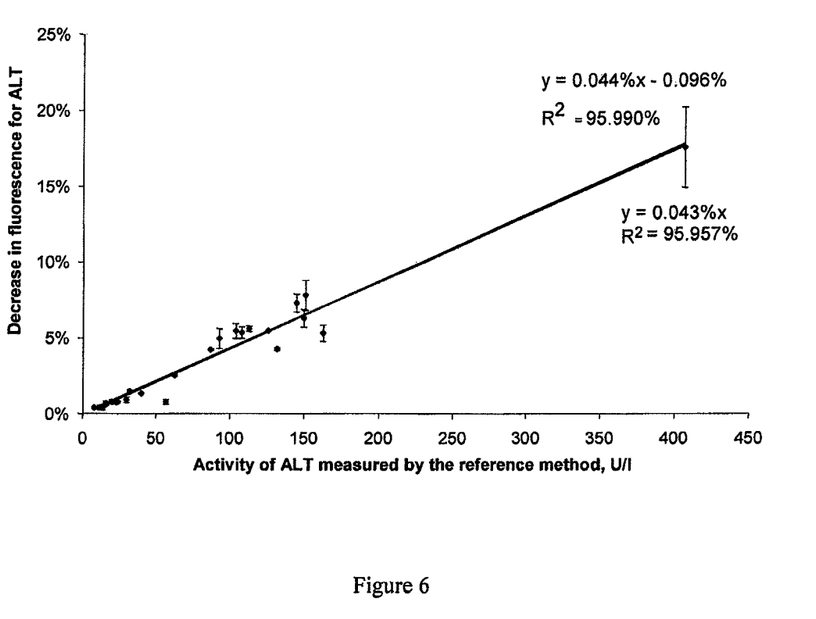
FIG. 6 is a graph representing the correlation between the decrease in the fluorescence of NADH measured by the method of the invention and the ALT activity measured by the reference method (Cobas automated machine). "Black" straight line has the equation y=ax+b; "gray" straight line has the equation y=ax.

2.2. Correlation Between the Reference Assay Method and the Assay Method According to the Present Invention 2.2.1. For ALT:

The results obtained are presented in FIG. 6. The correlation is linear. It is correct on the entire range studied, with linear regression coefficients greater than 0.959.

Figure 7:
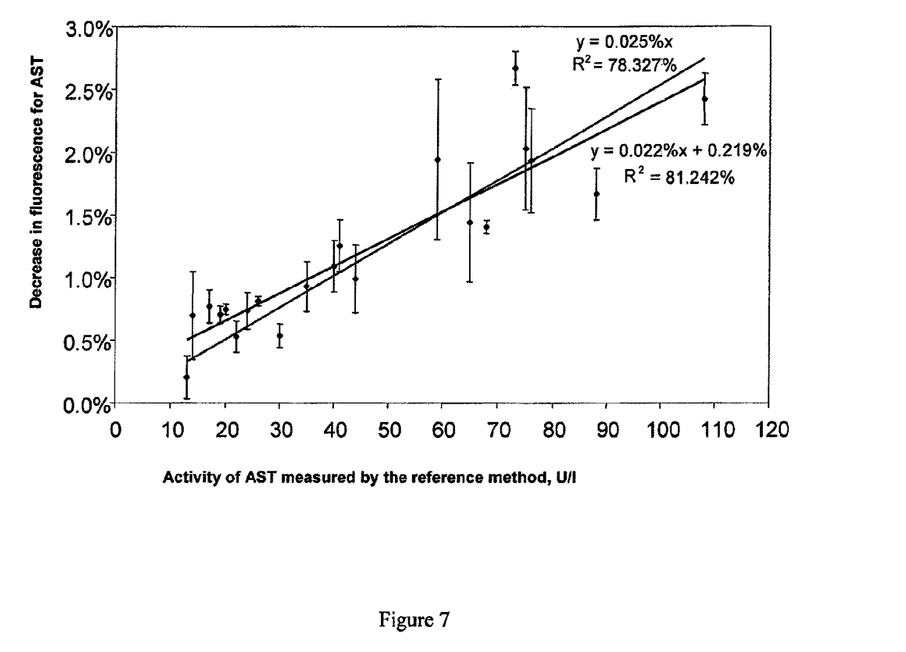
FIG. 7 is a graph representing the correlation between the decrease in the fluorescence of NADH measured by the method of the invention and the AST activity measured by the reference method (Cobas automated machine). "Black" straight line has the equation y=ax+b; "gray" straight line has the equation y=ax.

2.2.2. For AST:

The results obtained are presented in FIG. 7. The correlation is linear with $R^2$ values of 0.812 and 0.783 respectively for a linear regression of the type y=ax+b and a linear regression of the type y=ax. It is also noted that the variations in signal obtained for the assay of AST are twice as low as those determined for ALT. For example, for a transaminase activity of 100 U/L, a decrease in fluorescence for ALT is 5%, whereas it is only 2.5% for AST.

It was therefore checked if it was possible to improve this decrease in signal by testing two parameters capable of influencing these results: the quantity of NADH (45 μM instead of 90 μM) and the latent period (30 s instead of 90 s). The results obtained are presented in FIG. 8.

Figure 8:
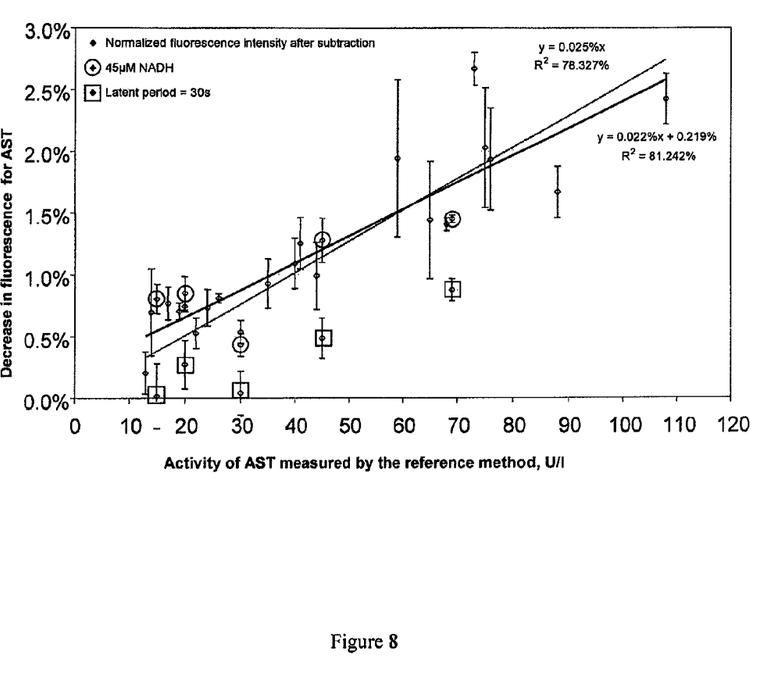
FIG. 8 is a graph representing the correlation between the decrease in the fluorescence of NADH measured by the method of the invention and the AST activity measured by the reference method (Cobas automated machine). The correlation takes into account only the values obtained under the optimum conditions (90 µM of NADH and a latent period of 90 seconds). The values obtained with 45 µM of NADH and the values obtained with the latent period of 30 s are nevertheless represented on the graph in order to estimate their correspondence with the straight line obtained. "Black" straight line has the equation y=ax+b; "gray" straight line has the equation y=ax.

It is evident from the graph of FIG. 8 that the decrease in the concentration of NADH from 90 μM to 45 μM does not make it possible to increase the decrease in fluorescence: the values obtained are of the same order of magnitude as those observed with 90 μM of NADH. It is nevertheless interesting to note that the CVs are better with 45 μM of NADH: indeed, under these conditions, the values of the 5 CVs vary between 0.6% and 10.5%. Thus, even if the decrease in the concentration does not make it possible to obtain larger decreases in the fluorescence, it allows a better repeatability.

Moreover, a latent period of 30 s instead of 90 s did not make it possible to improve the results. On the contrary, the decreases in fluorescence were greater under these conditions.

2.3. Effect of the Hematocrit

The hematocrit could constitute a parameter which impacts the measurements of fluorescence. Indeed, the measurement of the fluorescence of NADH is carried out on whole blood, therefore in the presence of red blood cells. Variable hematocrit levels in various patients with otherwise identical transaminase levels could therefore give different transaminase assay results because of the variation in absorption due to the variable quantities of red blood cells.

In order to verify this hypothesis, the effect of the hematocrit on the measurements of the decrease in fluorescence was tested. Various patients who were analyzed had hematocrit levels of between 21.6% and 51% (mean=34.3%, standard deviation=7.3%). Taking into account the available hematocrit range, various classes were defined:

hematocrit<25%
25%<hematocrit<35%
35%<hematocrit<45%
hematocrit>45%

Figure 9:
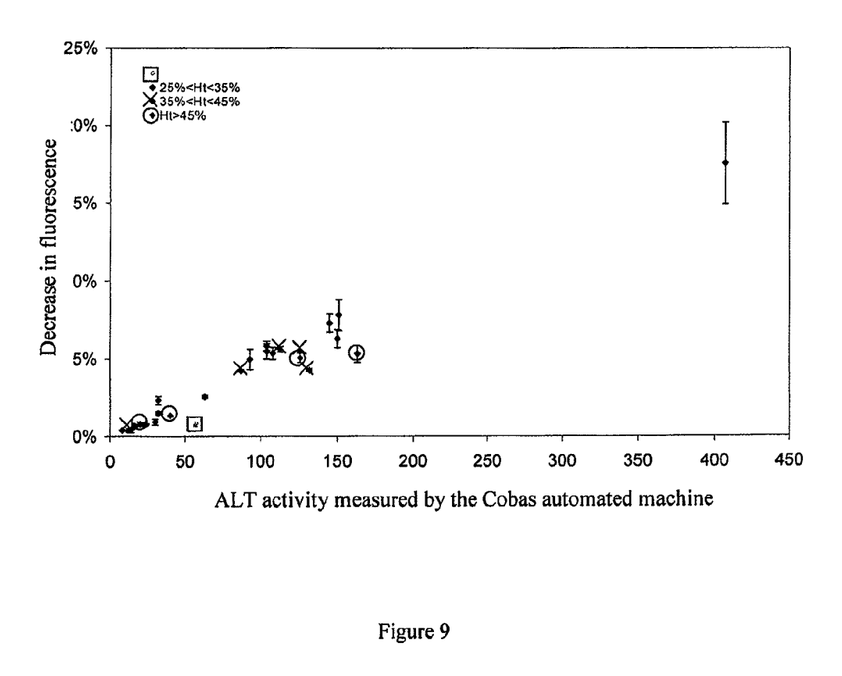
FIG. 9 is a graph representing the correlation between the measurement of the decrease in fluorescence measured by the method of the invention and the AST activity measured by the reference method (Cobas automated machine, Roche) as a function of the various classes of hematocrit (hematocrit<25%; 25%<hematocrit<35%; 35%<hematocrit<45% and hematocrit>45%).

The results obtained are presented in FIG. 9. These results do not demonstrate a trend between the different values of decrease in fluorescence that are measured and the hematocrit value. It can only be noted that the patient having the lowest hematocrit level appears to be outside the correlation.

No effect of the hematocrit is therefore observed on the measurements of the decrease in the fluorescence of NADH.

The invention claimed is:

1. A method for assaying, in a biological liquid sample, an NADH-dependent catalytic plasma enzyme ($E_N$), by measuring its enzymatic activity, comprising a step of measuring the decrease in the fluorescence of the NADH, in which method said biological liquid is whole blood and the enzymatic activity of said catalytic enzyme is measured by monitoring the decrease in the fluorescence of the NADH in a microfluidic chamber having a thickness of 20 μm to 2 mm.

2. The method as claimed in claim 1, wherein said catalytic enzyme is selected from the group consisting of lactate dehydrogenase (LDH), malate dehydrogenase (MDH) and isocitrate dehydrogenase (IDH).

3. A method for assaying, in a sample of biological liquid, a catalytic plasma enzyme ($E_C$) having $S_1$ and $S_2$ as substrates, by measuring the enzymatic activity of said enzyme $E_C$, comprising at least the following steps: a) incubation of said biological liquid with said substrate $S_1$, NADH, one or more different NADH-dependent catalytic enzymes ($E_N$) each having as substrate one of the products of the enzymatic reaction catalyzed by $E_C$, and optionally pyridoxal phosphate (PLP); b) addition of said substrate $S_2$ so as to initiate the enzymatic reactions catalyzed by the catalytic enzymes $E_C$ and $E_N$; in which method:

said biological liquid is whole blood,
after the addition of the substrate $S_2$ in step b), the mixture obtained is immediately introduced into a microfluidic chamber 20 μm to 2 mm thick, and the enzymatic activity of said catalytic enzyme $E_C$ is measured by monitoring the decrease in the fluorescence of NADH in said microfluidic chamber.

4. The method as claimed in claim 1, wherein the thickness of said microfluidic chamber is between 30 μm and 50 μm, preferably 30 μm.

5. The method as claimed in claim 1, wherein said microfluidic chamber comprises two walls, substantially parallel and separated by one or more means of keeping apart, such that a distance between said two walls is between 20 μm and 2 μm.

6. The method as claimed in claim 5, wherein at least one of the two walls comprises a material reflecting fluorescence light.

7. The method as claimed in claim 6, wherein said reflective material is silicon or a silicon oxide or nitride.

8. The method as claimed in claim 1, wherein the measurement of the decrease in fluorescence is carried out after a latent time has elapsed, defined by the sedimentation time of the red blood cells in said microfluidic chamber.

9. The method as claimed in claim 1, wherein the fluorescence of NADH is measured at a wavelength of between 420 nm and 550 nm, after excitation of the NADH at a wavelength of between 300 and 400 nm.

10. The method as claimed in claim 1, wherein the volume of the whole-blood sample is between 0.1 μL and 50 μL.

11. The method as claimed in claim 3, wherein the incubation time in step a) is between 2 and 30 minutes.

12. The method as claimed in claim 3, wherein the concentration of NADH in the mixture obtained in step a) is 20 μM to 250 μM.

13. The method as claimed in claim 3, wherein said catalytic enzyme $E_C$ is selected from the group consisting of aspartate aminotransferase (AST), alanine aminotransferase (ALT), pyruvate kinase, creatine kinase and glycerol kinase.

14. The method as claimed in claim 3, wherein said catalytic enzyme $E_C$ is aspartate aminotransferase, said substrate $S_1$ is L-aspartate, said substrate $S_2$ is α-ketoglutarate, and said catalytic enzymes $E_N$ are a malate dehydrogenase (MDH), or an MDH and a lactate dehydrogenase (LDH).

15. The method as claimed in claim 3, wherein said catalytic enzyme $E_C$ is alanine aminotransferase, said substrate $S_1$ is L-alanine, said substrate $S_2$ is α-ketoglutarate, and said catalytic enzyme $E_N$ is a lactate dehydrogenase.

* * * * *

UNITED STATES PATENT AND TRADEMARK OFFICE
CERTIFICATE OF CORRECTION

PATENT NO. : 8,426,156 B2  
APPLICATION NO. : 12/763395  
DATED : April 23, 2013  
INVENTOR(S) : Cubizolles et al.

It is certified that error appears in the above-identified patent and that said Letters Patent is hereby corrected as shown below:

In the Specifications:

Column 9,  
Line 1, "$\geqq 990\%$" should read --$\geq 99\%$--.

In the Claims:

Column 15,  
Line 10, "2 μm" should read --2 mm--.

Signed and Sealed this  
Thirteenth Day of August, 2013

Teresa Stanek Rea  
*Acting Director of the United States Patent and Trademark Office*